United States Patent
Ioka

(10) Patent No.: US 12,100,148 B2
(45) Date of Patent: Sep. 24, 2024

(54) IMAGE PROCESSING APPARATUS, IMAGE PROCESSING SYSTEM, IMAGE PROCESSING METHOD, AND COMPUTER-READABLE RECORDING MEDIUM

(71) Applicant: EVIDENT CORPORATION, Tatsuno-machi (JP)

(72) Inventor: Ken Ioka, Hachioji (JP)

(73) Assignee: Evident Corporation, Nagano (JP)

( * ) Notice: Subject to any disclaimer, the term of this patent is extended or adjusted under 35 U.S.C. 154(b) by 349 days.

(21) Appl. No.: 17/726,933

(22) Filed: Apr. 22, 2022

(65) Prior Publication Data

US 2022/0245808 A1 Aug. 4, 2022

Related U.S. Application Data

(63) Continuation of application No. PCT/JP2019/044889, filed on Nov. 15, 2019.

(51) Int. Cl.
| | | |
|---|---|---|
| G06T 7/00 | (2017.01) | |
| G01N 21/25 | (2006.01) | |
| G01N 21/27 | (2006.01) | |
| G06T 7/62 | (2017.01) | |
| G06V 10/74 | (2022.01) | |

(52) U.S. Cl.
CPC ......... *G06T 7/0012* (2013.01); *G01N 21/256* (2013.01); *G01N 21/27* (2013.01);
(Continued)

(58) Field of Classification Search
CPC ............. G06T 7/0012; G06T 7/62; G06T 2207/10152; G06T 2207/30024;
(Continued)

(56) References Cited

U.S. PATENT DOCUMENTS

| | | | | |
|---|---|---|---|---|
| 2009/0274351 A1* | 11/2009 | Otsuka | .................... | G06V 10/56 |
| | | | | 382/128 |
| 2010/0195903 A1* | 8/2010 | Tani | ..................... | G06V 20/693 |
| | | | | 382/162 |

(Continued)

FOREIGN PATENT DOCUMENTS

| | | |
|---|---|---|
| JP | 2006-292582 A | 10/2006 |
| JP | 2010156612 A | 7/2010 |

(Continued)

OTHER PUBLICATIONS

International Search Report dated Feb. 18, 2020 received in PCT/JP2019/044889, (2020).

(Continued)

*Primary Examiner* — Juan A Torres
(74) *Attorney, Agent, or Firm* — Scully, Scott, Murphy & Presser, P.C.

(57) ABSTRACT

An image processing apparatus includes a processor including hardware. The processor is configured to: acquire a first wavelength image and a second wavelength image, the first wavelength image being generated by irradiating a stage and by capturing light that has passed through the stage, the second wavelength image being generated by irradiating a specimen and by capturing light that has passed through the stage and the specimen, the specimen including a core tissue; calculate a spectral transmittance image; cause a display to display at least one of the spectral transmittance image and the second wavelength image as a display image; extract an area of the spectral transmittance image having spectral transmittance similar to spectral transmittance of a reference area in the display image as a core tissue area of the core tissue; and calculate an amount of the core tissue area.

19 Claims, 11 Drawing Sheets

(52) U.S. Cl.
CPC .............. *G06T 7/62* (2017.01); *G06V 10/761* (2022.01); *G06T 2207/10152* (2013.01); *G06T 2207/30024* (2013.01)

(58) Field of Classification Search
CPC ........... G06T 2207/10016; G06T 2207/10024; G01N 21/256; G01N 21/27; G01N 33/48; G01N 33/483; G06V 10/761; G06V 2201/03; G06V 10/143; G06V 10/762
USPC .......................................................... 382/128
See application file for complete search history.

(56) References Cited

U.S. PATENT DOCUMENTS

| | | | | |
|---|---|---|---|---|
| 2010/0322502 | A1* | 12/2010 | Otsuka | G06V 20/695 382/133 |
| 2012/0082364 | A1* | 4/2012 | Tani | G06T 7/90 382/133 |
| 2020/0320698 | A1 | 10/2020 | Ioka | |
| 2021/0027464 | A1 | 1/2021 | Ioka | |

FOREIGN PATENT DOCUMENTS

| | | |
|---|---|---|
| JP | 2013-253861 A | 12/2013 |
| WO | 2019/111365 A1 | 6/2019 |
| WO | 2019/202646 A1 | 10/2019 |

OTHER PUBLICATIONS

Washita, T., MD, PhD., et al., Macroscopic on-site quality evaluation of biopsy specimens to improve the diagnostic accuracy during EUS-guided FNA using a 19-gauge needle for solid lesions: a single prospective pilot study (MOSE study), Gastrointestinal Endoscopy, vol. 81, No. 1, 12015, pp. 177-185, (2015).

* cited by examiner

IMAGE PROCESSING APPARATUS, IMAGE PROCESSING SYSTEM, IMAGE PROCESSING METHOD, AND COMPUTER-READABLE RECORDING MEDIUM

CROSS-REFERENCE TO RELATED APPLICATION

This application is a continuation of International Application No. PCT/JP2019/044889, filed on Nov. 15, 2019, the entire contents of which are incorporated herein by reference.

BACKGROUND

1. Technical Field

The present disclosure relates to analyses of biopsies, particularly, specimens including biological tissues obtained from endoscopic needle biopsies.

2. Related Art

In an intraoperative rapid cytological diagnosis by biopsy, particularly, endoscopic needle biopsy, a specimen discharged to a petri dish is sometimes buried under blood and is also in a knotted state by getting entangled with other tissues. Consequently, in macroscopic on-site evaluation (MOSE) that is a process of performing macroscopic evaluation on a biopsy specimen, a doctor loosen the knot by using tweezers or the like and separate living tissue of the target organ, what is called "core tissue", needed for a pathological diagnosis from the other biological tissues, and then measures an amount of the core tissue, thereby determining, on the basis of this measurement result, whether or not a specimen is to be obtained again (for example, see Takuji Iwashita, Ichiro Yasuda, "Macroscopic on-site quality evaluation of biopsy specimens to improve the diagnostic accuracy during EUS-guided FNA using a 19-gauge needle for solid lesions: a single-center prospective pilot study (MOSE study)" GASTROINTESTINAL ENDOSCOPY, Volume 81, NO. 1, 12015, pp. 177-185).

SUMMARY

In some embodiments, an image processing apparatus includes a processor including hardware. The processor is configured to: acquire a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculate a spectral transmittance image based on the first wavelength image and the second wavelength image; cause a display to display at least one of the spectral transmittance image and the second wavelength image as a display image; extract, based on a designation signal for designating a reference area in the display image, an area of the spectral transmittance image having spectral transmittance similar to spectral transmittance of the reference area as a core tissue area of the core tissue; and calculate an amount of the core tissue area.

In some embodiments, an image processing apparatus includes a processor including hardware. The processor is configured to: acquire a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculate a spectral transmittance image based on the first wavelength image and the second wavelength image; calculate a spectral vector of each of pixels included in the spectral transmittance image; classify each of the pixels included in the spectral transmittance image into at least two or more groups based on a degree of similarity between the spectral vector of each of the pixels and a reference vector; set, from among a plurality of blocks obtained by dividing the spectral transmittance image into each of predetermined pixels, an area of a block that has a large number of pixels that belongs to a group that has a high degree of similarity to the reference vector as a reference area; extract an area of the spectral transmittance image having spectral transmittance similar to spectral transmittance of the reference area as a core tissue area of the core tissue; and calculate an amount of the core tissue area.

In some embodiments, an image processing system includes: the image processing apparatus; a light source configured to irradiate illumination light in a wavelength band in a switchable manner; an imager configured to capture light that has passed through the stage; and a controller configured to cause the first wavelength image to be generated by causing the light source to irradiate the illumination light in a state in which the specimen is not mounted on the stage and by causing the imager to capture an image, and cause the second wavelength image to be generated by causing the light source to irradiate the illumination light in the state in which the specimen is mounted on the stage and by causing the imager to capture an image.

In some embodiments, provided is an image processing method performed by an image processing apparatus. The method includes: acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculating a spectral transmittance image based on the first wavelength image and the second wavelength image; causing a display to display at least one of the spectral transmittance image and the second wavelength image as a display image; extracting, based on a designation signal for designating a reference area in the display image, an area of the spectral transmittance image having spectral transmittance similar to spectral transmittance of the reference area as a core tissue area of the core tissue; and calculating an amount of the core tissue area.

In some embodiments, provided is an image processing method performed by an image processing apparatus. The method includes: acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculating a spectral transmittance image based on the first wavelength image and the second wavelength image; calculating a spectral vector of each of pixels included in the spectral transmittance image; classifying each of the pixels included in the spectral transmittance image into at least two or more groups based on a degree of similarity between the spectral vector of each of the pixels and a reference vector; setting, from among a plurality of blocks obtained by dividing the spectral transmittance image into each of predetermined pixels, an area of a block that has a large number of pixels that belongs to a group that has a high degree of similarity to the reference vector as a reference area; extracting an area of the spectral transmittance image having spectral transmittance similar to spectral transmittance of the reference area as a core tissue area of the core tissue; and calculating an amount of the core tissue area.

In some embodiments, provided is a non-transitory computer-readable recording medium with an executable program stored thereon. The program causes an image processing apparatus to perform: acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculating a spectral transmittance image based on the first wavelength image and the second wavelength image; causing a display to display at least one of the spectral transmittance image and the second wavelength image as a display image; extracting, based on a designation signal for designating a reference area in the display image, an area of the spectral transmittance image having spectral transmittance similar to spectral transmittance of the reference area as a core tissue area of the core tissue; and calculating an amount of the core tissue area.

In some embodiments, provided is a non-transitory computer-readable recording medium with an executable program stored thereon. The program causes an image processing apparatus to perform: acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue; calculating a spectral transmittance image based on the first wavelength image and the second wavelength image; calculating a spectral vector of each of pixels included in the spectral transmittance image; classifying each of the pixels included in the spectral transmittance image into at least two or more groups based on a degree of similarity between the spectral vector of each of the pixels and a reference vector; setting, from among a plurality of blocks obtained by dividing the spectral transmittance image into each of predetermined pixels, an area of a block that has a large number of pixels that belongs to a group that has a high degree of similarity to the reference vector as a reference area; extracting an area of the spectral transmittance image having spectral transmittance similar to spectral transmittance of the reference area as a core tissue area of the core tissue; and calculating an amount of the core tissue area.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
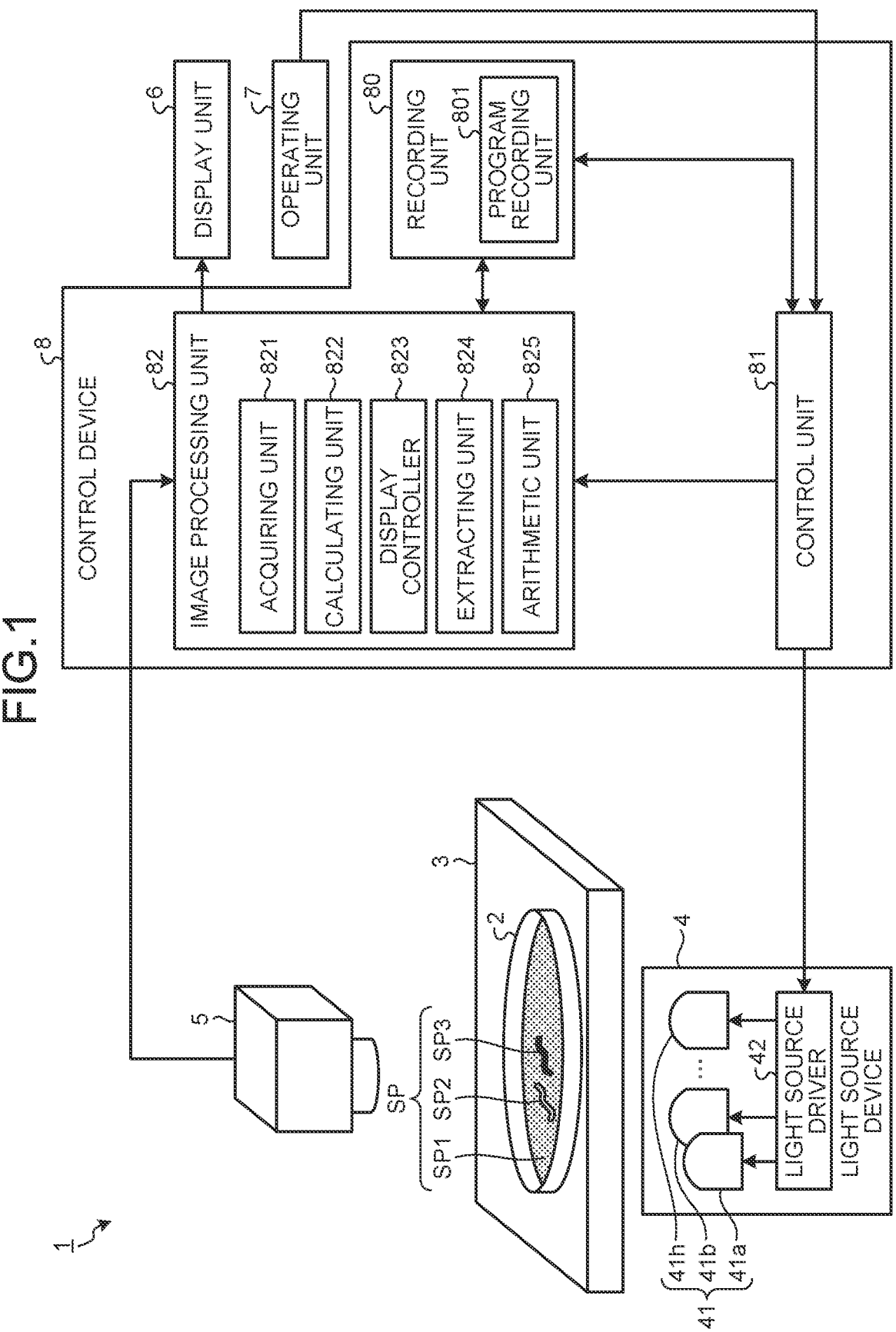
FIG. 1 is a schematic diagram illustrating a schematic configuration of an image processing system according to a first embodiment.

In the following, modes for carrying out the present disclosure (hereinafter, referred to as "embodiments") will be described. In the present embodiments, a description will be given by using, as an example, an image processing system that determines an amount of core tissue of a specimen obtained from a biopsy. Furthermore, the present disclosure is not limited by the embodiments described below. Moreover, in the drawings, components that are identical to those in embodiments are assigned the same reference numerals.

First Embodiment

Configuration of Image Processing System

FIG. 1 is a schematic diagram illustrating a schematic configuration of an image processing system according to a first embodiment. An image processing system 1 illustrated in FIG. 1 determines whether or not an amount of tissue of core tissue of a specimen SP contained in a specimen vessel 2, such as a petri dish, is larger than or equal to a threshold. The image processing system 1 includes a stage 3, a light source device 4, an imaging device 5, a display unit 6, an operating unit 7, and a control device 8. Furthermore, in the first embodiment, the stage 3, the light source device 4, the imaging device 5, the display unit 6, the operating unit 7, and the control device 8 are bi-directionally connected in a wired manner so as to be able to communicate with each other; however, the connection is not limited to this and may be bi-directionally connected by wireless communication so as to be able to communicate with each other.

The stage 3 includes a mounting surface on which the specimen vessel 2 is to be mounted. The stage 3 is constituted by using a transparent member formed of, for example, plastic, glass, or the like, and transmits illumination light illuminated by the light source device 4 that will be described later. Furthermore, the constitution or the material of the stage 3 may be appropriately changed in accordance with the position of the light source device 4. Furthermore, the stage 3 may be movably provided in a horizontal direction (an X-direction and a Y-direction) and a vertical direction based on a predetermined position.

The light source device 4 irradiates, under the control of the control device 8, multiband illumination light toward the stage 3. The light source device 4 includes a plurality of light source units 41 and a light source driver 42.

The plurality of light source units 41 irradiate a plurality of pieces of illumination light each having a different wavelength band. Specifically, the plurality of light source units 41 include a first light source 41a to an eighth light source 41h. Each of the first light source 41a to the eighth light source 41h includes a light emitting diode (LED) element, a filter that transmits a predetermined wavelength band of light emitted by the associated LED element, and an optical system that performs irradiation by focusing light that passes through the filter. The light source driver 42 supplies a current to any one or more of the plurality of light source units 41 under the control of the control device 8.

Figure 2:
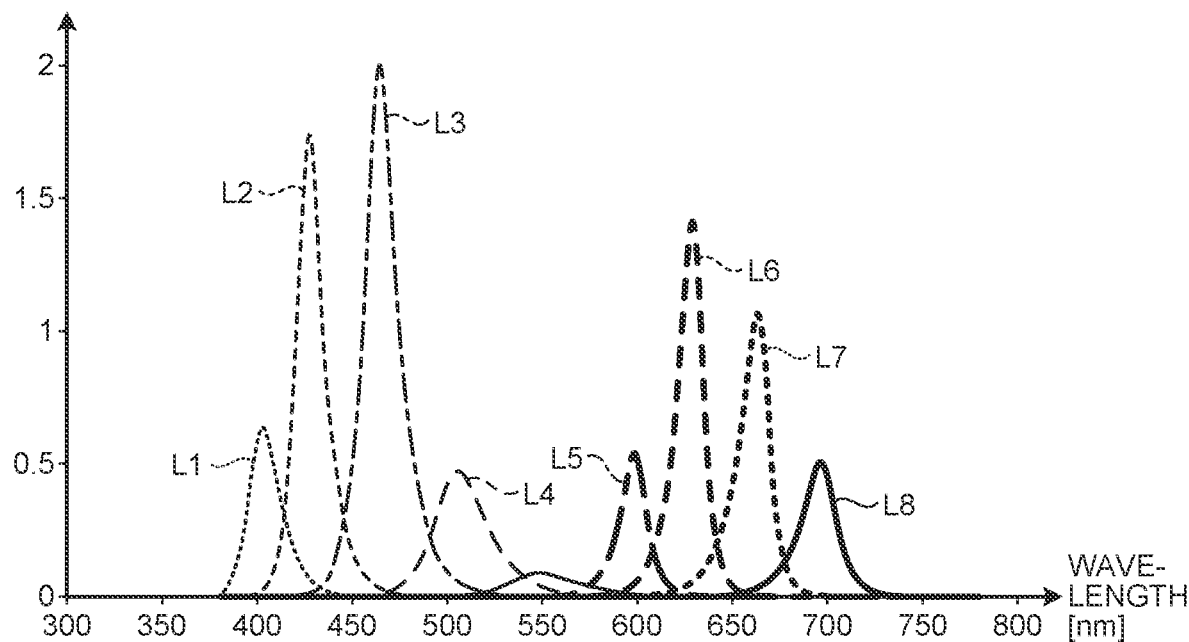
FIG. 2 is a diagram schematically illustrating spectral characteristics of illumination light illuminated by a light source device according to the first embodiment.

In the following, the spectral characteristics of the illumination light irradiated by the light source device 4 will be described. FIG. 2 is a diagram schematically illustrating the spectral characteristics of the illumination light irradiated by the light source device 4. In FIG. 2, the horizontal axis indicates a wavelength (nm) and the vertical axis indicates an intensity. Furthermore, a curve $L_1$ indicates the spectral characteristic of the first light source 41a, a curve $L_2$ indicates the spectral characteristic of the second light source 41b, a curve $L_3$ indicates the spectral characteristic of the third light source 41c, a curve $L_4$ indicates the spectral characteristic of the fourth light source 41d, the curve $L_5$ indicates the spectral characteristic of the fifth light source 41e, a curve $L_6$ indicates the spectral characteristic of the sixth light source 41f, a curve $L_7$ indicates the spectral characteristic of the seventh light source 41g, and a curve $L_8$ indicates the spectral characteristic of the eighth light source 41h.

As illustrated in FIG. 2, under the control of the control device 8, the light source device 4 emits any one or more of the first light source 41a to the eighth light source 41h, thereby irradiating multiband and narrow band illumination light toward the stage 3. For example, under the control of the control device 8, the light source device 4 emits the fifth light source 41e as indicated by the curve $L_5$, thereby irradiating narrow band illumination light that has an umber color and that has a peak at 600 nm. In this case, the contrast between blood and other tissues becomes high, so that it is possible to easily observe the core tissue of the specimen SP.

The imaging device 5 generates image data (hereinafter, referred to as a "first wavelength image") by capturing, under the control of the control device 8, the illumination light that is irradiated by the light source device 4 and that has been transmitted through at least the stage 3 in a state in which the specimen vessel 2 is not mounted on the stage 3. Furthermore, the imaging device 5 generates image data (hereinafter, referred to as a "second wavelength image") by capturing, under the control of the control device 8, the illumination light that is irradiated by the light source device 4 and that has been transmitted through at least both of the stage 3 and the specimen SP in a state in which the specimen vessel 2 having contained therein the specimen SP is mounted on the stage 3. The imaging device 5 outputs the first wavelength image and the second wavelength image to the control device 8. The imaging device 5 is constituted by using an optical system that is constituted by at least a lens that forms an image of a subject, an image sensor, such as a charge coupled device (CCD) or a complementary metal oxide semiconductor (CMOS), and an image processing circuit, such as an application specific integrated circuit (ASIC) or a field programmable gate array (FPGA).

Figure 3:
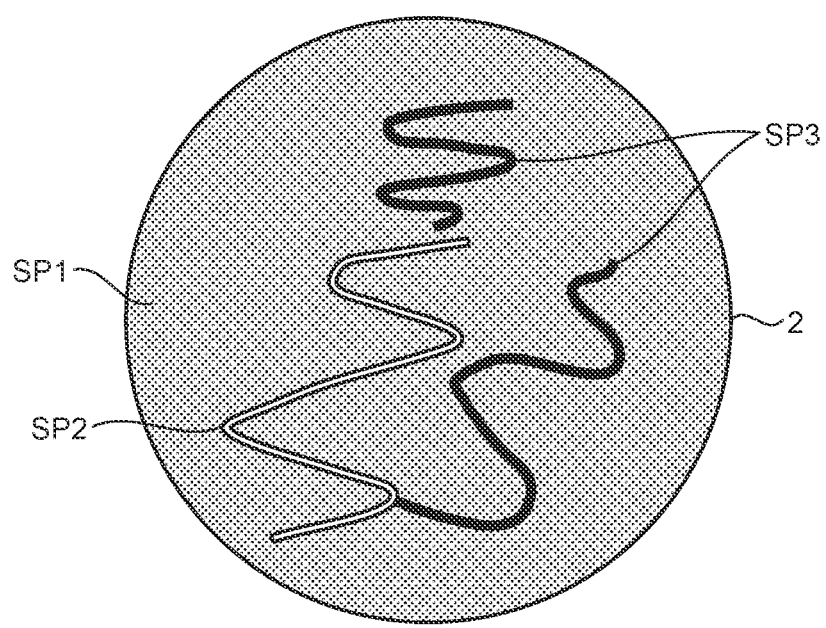
FIG. 3 is a diagram illustrating an example of a display image displayed by a display unit according to the first embodiment.

The display unit 6 displays a live view image or a display image associated with the image data that is input from the control device 8. For example, the display unit 6 displays, as illustrated in FIG. 3, an image P1 associated with the image data that is input from the control device 8. The image P1 includes blood SP1 that is separated from the specimen SP that is contained in the specimen vessel 2, core tissue SP2 (red tissue), and biological tissue SP3 (white tissue) that is other than the core tissue SP2. The display unit 6 is constituted by using a display panel, such as a liquid crystal panel or an organic electro luminescence (EL) panel.

The operating unit 7 receives various inputs related to the image processing system 1, and outputs the received operation to the control device 8. The operating unit 7 receives an operation for designating a wavelength band irradiated by the light source device 4 or an input of a mode, and then, outputs the received operation content to the control device 8. The operating unit 7 is constituted by using a touch panel, a switch, a button, a keyboard, a mouse, a foot switch, and the like. Furthermore, a voice input performed by using a microphone or the like may be applicable for the operating unit 7. Of course, the operating unit 7 may be constituted by using an imaging device, a line-of-sight detection circuit that detects a line of sight of a user included in the image data, and the like, and may receive a line of sight of the user, such as an input in accordance with, for example, a staying time.

The control device 8 perform control of each of the units included in the image processing system 1. The control device 8 includes a recording unit 80, a control unit 81, and an image processing unit 82.

The recording unit 80 records various kinds of information related to the image processing system 1, image data that has been subjected to image processing performed by the image processing unit 82, and the like. Furthermore, the recording unit 80 includes a program recording unit 801 that records various programs executed by the image processing system 1. The recording unit 80 is constituted by using a volatile memory, a nonvolatile memory, a solid state drive (SSD), a hard disk drive (HDD), or the like.

The control unit 81 perform control of each of the units constituting the image processing system 1. Furthermore, the control unit 81 performs control of the wavelength band of the illumination light irradiated by the light source device 4 in accordance with an operation received by the operating unit 7. The control unit 81 is constituted by using a memory and a processor that includes hardware, such as a central processing unit (CPU). Furthermore, the control unit 81 causes the light source device 4 to irradiate illumination light in a state in which the specimen vessel 2 having contained therein the specimen SP is not mounted on the stage 3, and also, causes the imaging device 5 to capture an image and generate the first wavelength image. Furthermore, the control unit 81 causes the light source device 4 to irradiate illumination light in a state in which the specimen vessel 2 having contained therein the specimen SP is mounted on the stage 3, and also, causes the imaging device 5 to capture an image and generate the second wavelength image.

The image processing unit 82 performs various kinds of image processing on the image data that is input from the imaging device 5, and then, outputs the processed image data to the display unit 6. The image processing unit 82 is constituted by using a memory, and a processor having hardware, such as a field programmable gate array (FPGA) or a graphics processing unit (GPU). The image processing unit 82 includes an acquiring unit 821, a calculating unit 822, a display controller 823, an extracting unit 824, and an arithmetic unit 825. Furthermore, in the first embodiment, the image processing unit 82 functions as an image processing apparatus.

The acquiring unit 821 acquires the first wavelength image and the second wavelength image that are generated by the imaging device 5. Specifically, the acquiring unit 821 acquires the first wavelength image that is generated by irradiating the stage 3, which is capable of transmitting light, with illumination light in a predetermined wavelength band, and also, capturing the light that has passed through the stage 3. Furthermore, the acquiring unit 821 acquires the second wavelength image that is generated by irradiating the specimen that is the specimen SP, which has been acquired by a biopsy and includes the core tissue, and that is mounted on the stage 3 with illumination light in a predetermined wavelength band, and also, capturing the light that has passed through both of the stage 3 and the specimen SP. Here, the acquiring unit 821 acquires the first wavelength image at the time of capturing an image of the specimen SP; however, the first wavelength image may be acquired in advance and recorded in an external memory or the like, and then, this recorded data may be read.

The calculating unit 822 generates a spectral transmittance image by calculating the spectral transmittance image on the basis of the first wavelength image and the second wavelength image. Here, the spectral transmittance image indicates an image obtained by calculating a spectral transmittance of each of the wavelength bands in the respective pixels. Specifically, the calculating unit 822 calculates the spectral transmittance of each of the wavelength bands in the respective pixels by dividing the second wavelength image by the first wavelength image.

The display controller 823 causes the display unit 6 to display, as a display image, at least one of the second wavelength image and the spectral transmittance image that is generated by the calculation performed by the calculating unit 822. Furthermore, the display controller 823 displays various kinds of information related to the image processing system 1.

The extracting unit 824 extracts, on the basis of a designation signal for designating a reference area in the display image that is received by the operating unit 7 in accordance with an operation performed by a user, an area of the spectral transmittance image having the spectral transmittance similar to that of the reference area as a core tissue area of the core tissue.

The arithmetic unit 825 calculates, by performing an arithmetic operation, an amount of the core tissue area extracted by the extracting unit 824. For example, the arithmetic unit 825 obtains a square measure of the core tissue area included in the specimen SP by using the square measure of the pixels that are extracted as the core tissue area from among the pixels on the image sensor included in the imaging device 5 and using the magnification of the optical system included in the imaging device 5, and then, the value of this square measure is set to be an amount of the core tissue area. Alternatively, the arithmetic unit 825 may calculate a length as an amount of the core tissue area by using the same arithmetic operation described above.

Process Performed by Image Processing System

Figure 4:
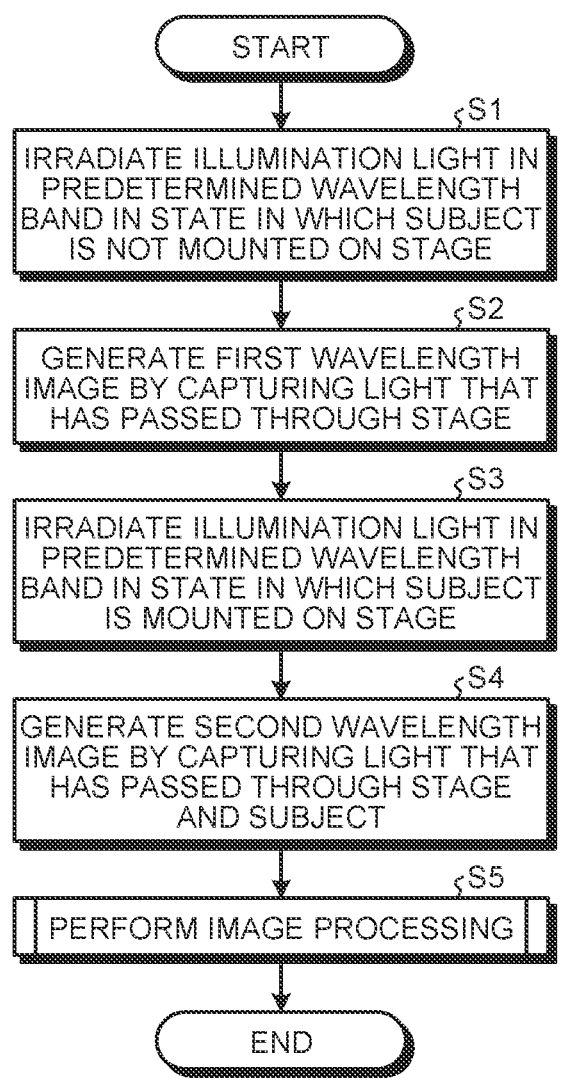
FIG. 4 is a flowchart illustrating, in outline, a process performed by the image processing system according to the first embodiment.

In the following, a process performed by the image processing system 1 will be described. FIG. 4 is a flowchart illustrating, in outline, the process performed by the image processing system 1.

As illustrated in FIG. 4, first, the control unit 81 causes the light source device 4 to irradiate illumination light in a predetermined wavelength band in a state in which the specimen vessel 2 is not mounted on the stage 3 (Step S1), and causes the imaging device 5 to generate the first wavelength image by capturing the light that has passed through the stage 3 (Step S2).

Subsequently, the control unit 81 causes the light source device 4 to irradiate the illumination light in the predetermined wavelength band in a state in which the specimen vessel 2 is mounted on the stage (Step S3), and causes the imaging device 5 to capture the light that has passed through the stage and the specimen SP, whereby the second wavelength image is generated (Step S4).

After that, the image processing unit 82 performs image processing for determining whether or not an amount of tissue of the core tissue of the specimen SP contained in the specimen vessel 2 is larger than or equal to the threshold (Step S5).

Image Processing

Figure 5:
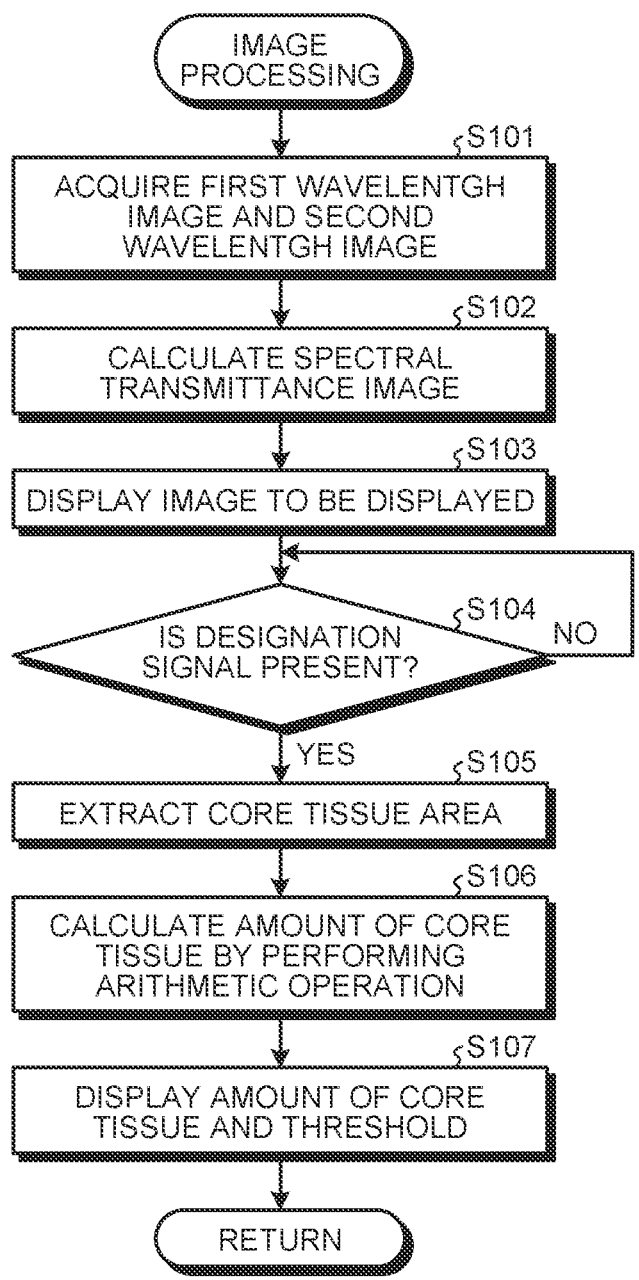
FIG. 5 is a flowchart illustrating, in outline, image processing performed in the process illustrated in FIG. 4.

FIG. 5 is a flowchart illustrating, in outline, the image processing performed in the process at Step S5 described above.

As illustrated in FIG. 5, first, the acquiring unit 821 acquires the first wavelength image and the second wavelength image from the imaging device 5 (Step S101).

Subsequently, the calculating unit 822 calculates the spectral transmittance image on the basis of the ratio between each of the wavelengths of the first wavelength image and each of the wavelengths of the second wavelength image (Step S102).

Subsequently, the display controller 823 causes the display unit 6 to display at least one of the spectral transmittance image and the second wavelength image (Step S103). Furthermore, in the following, a description will be made on the assumption that the display controller 823 causes the display unit 6 to continuously display the second wavelength image.

After that, if the designation signal for designating the reference area in the second wavelength image displayed by the display unit 6 is input from the operating unit 7 (Yes at Step S104), the extracting unit 824 extracts, as the core tissue area of the core tissue, an area of the spectral transmittance image having the spectral transmittance similar to that of the reference area in accordance with the instruction signal (Step S105). After the process at Step S105, the image processing unit 82 proceeds to the process at Step S106 that will be described later. In contrast, if the designation signal for designating the reference area in the second wavelength image displayed by the display unit 6 is not input from the operating unit 7 (No at Step S104), the image processing unit 82 repeats this determination until the instruction signal is input from the operating unit 7.

At Step S106, the arithmetic unit 825 calculates, by performing an arithmetic operation, an amount of the core tissue area extracted by the extracting unit 824. For example, the arithmetic unit 825 calculates, by performing an arithmetic operation, the square measure of the core tissue area included in the specimen SP by using the square measure of the pixels that are extracted as the core tissue area from among the pixels on the image sensor included in the imaging device 5 and using the magnification of the optical system included in the imaging device 5, and then, calculates, by performing an arithmetic operation, a value of this square measure as the amount of the core tissue area.

Subsequently, the display controller 823 causes the display unit 6 to display the amount of the core tissue area of the specimen SP calculated by the arithmetic unit 825 and the threshold (Step S107). Here, the threshold is the value indicating that the specimen need not to be recollected. As a result, an evaluator or a user is able to intuitively determine, with a simple operation, whether the amount of the tissue of the core tissue that is needed for a pathological diagnosis and that is included in the specimen SP obtained from a biopsy is sufficient. After the process at Step S107, the image processing system 1 returns to the main routine illustrated in FIG. 4 and ends the present image processing process.

According to the first embodiment described above, the display controller 823 causes the display unit 6 to display the threshold and the amount of the amount of the core tissue of the specimen SP calculated by performing the arithmetic operation performed by the arithmetic unit 825; therefore, it is possible for the evaluator or the user to determine, with the simple operation, whether or not the amount of the tissue of the core tissue that is needed for the pathological diagnosis and that is included in the specimen SP obtained from the biopsy is sufficient.

Furthermore, according to the first embodiment, it is possible to eliminate an error between the light source device 4 and the imaging device 5 caused by an absolute value and remove variations in image capturing, for example, a variation in light sources, a variation in each of the colors, a variation in caused by a positional relationship between the light source device 4 and the imaging device 5, so that it is possible to perform determination with high accuracy.

Furthermore, according to the first embodiment, the display controller 823 causes the display unit 6 to display the amount of the core tissue of the specimen SP and the threshold, so that the user is able to intuitively grasp the amount of the core tissue of the specimen SP.

Furthermore, according to the first embodiment, the display controller 823 causes the display unit 6 to display the amount of the core tissue of the specimen SP and the threshold, so that proficiency of the evaluator is not needed and it is thus possible to reduce the working hours.

Furthermore, according to the first embodiment, as the multiband illumination light irradiated by the light source device 4, illumination light that includes at least one narrow band light in a wavelength band in which a full width at half maximum is within range of 30 nm, for example, illumination light that includes a narrow band in a wavelength band of one of 415 nm, 430 nm, 465 nm, 505 nm, 545 nm, 600 nm, 630 nm, 660 nm, and 700 nm, as a peak is irradiated; therefore, in a case of, for example, 600 nm, it is possible to display the boundary between blood and solid tissue at a high contrast, and, in a case of 505 nm, if the color of blood is light, it is possible to display the boundary between the background and the solid tissue at a high contrast.

Modification of the First Embodiment

In the following, a modification of the first embodiment will be described. In the first embodiment described above, it is determined, by the evaluator or the user, whether or not the amount of the core tissue area is sufficient by displaying the amount of the core tissue area calculated by the arithmetic unit 825 and the threshold on the display unit 6; however, in the modification of the first embodiment, determination is performed by a control device. In a description below, a configuration of an image processing system according to the modification of the first embodiment is described, and then, image processing performed by the image processing system according to the modification of the first embodiment will be described. Furthermore, components that are identical to those in the image processing system 1 according to the first embodiment are assigned the same reference numerals and descriptions thereof in detail will be omitted.

Configuration of Image Processing System

Figure 6:
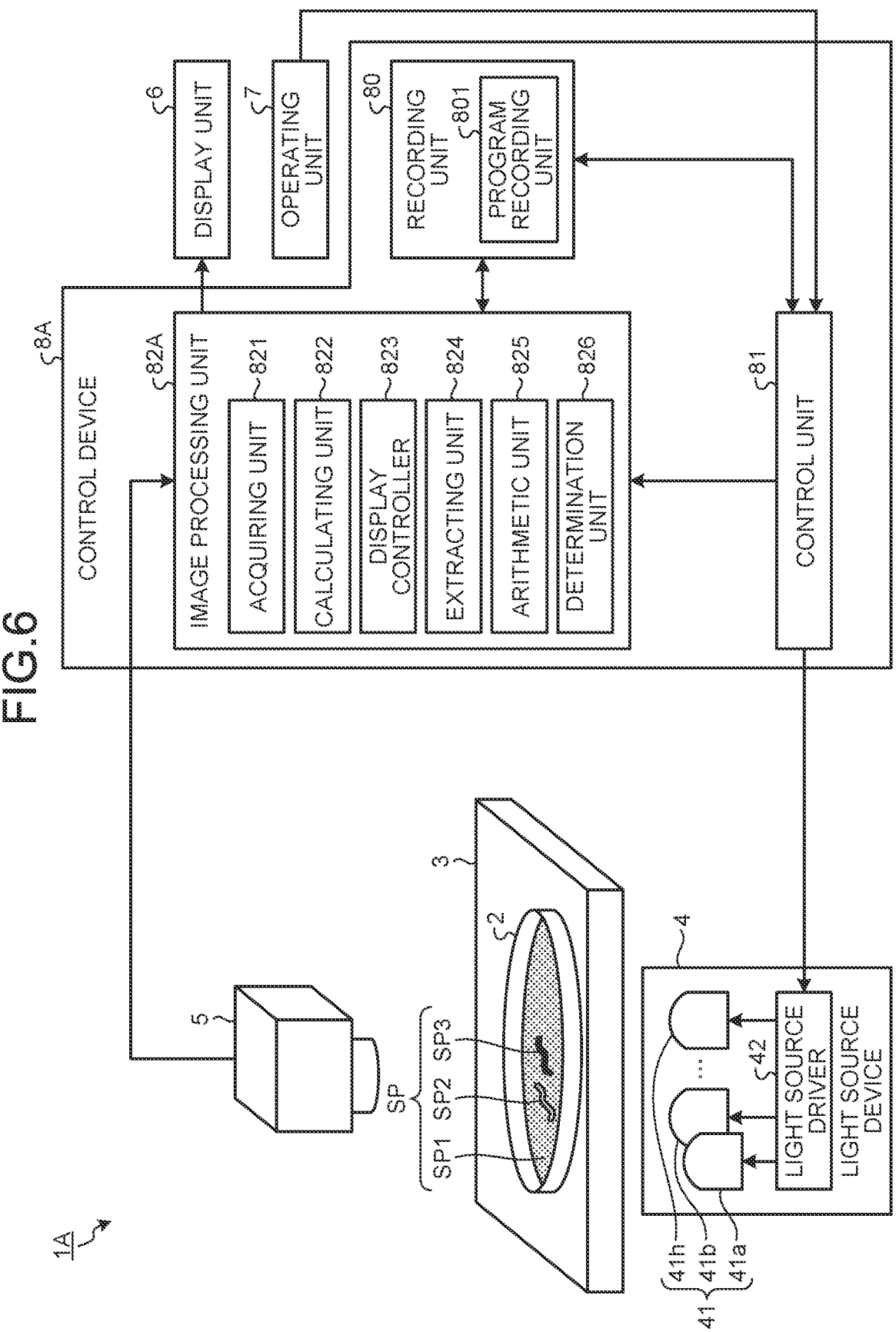
FIG. 6 is a schematic diagram illustrating a schematic configuration of an image processing system according to a modification of the first embodiment.

FIG. 6 is a schematic diagram illustrating a schematic configuration of an image processing system according to the modification of the first embodiment. An image processing system 1A illustrated in FIG. 6 includes a control device 8A instead of the control device 8 according to the first embodiment described above. The control device 8A includes an image processing unit 82A instead of the image processing unit 82 according to the first embodiment described above.

The image processing unit 82A is constituted by using a memory and a processor including hardware, such as a FPGA or a GPU. The image processing unit 82A further includes a determination unit 826 in addition to the configuration of the image processing unit 82 according to the first embodiment described above.

The determination unit 826 determines whether or not the amount of the core tissue area calculated by performing the arithmetic operation by the arithmetic unit 825 is larger than or equal to the threshold. Here, the threshold is a value indicating that the specimen need not be recollected.

Image Processing

Figure 7:
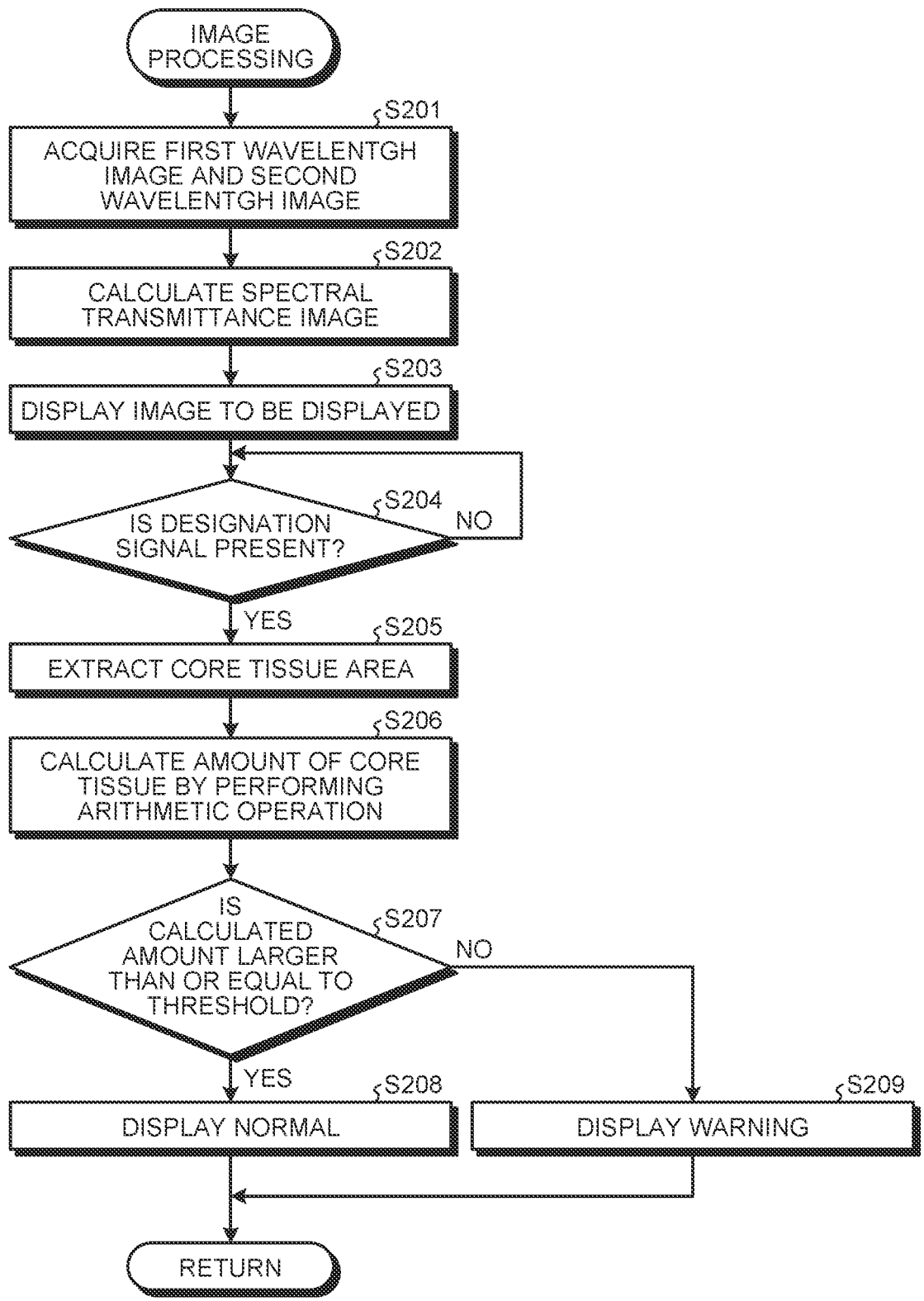
FIG. 7 is a flowchart illustrating, in outline, image processing performed by the image processing unit according to the modification of the first embodiment.

FIG. 7 is a flowchart illustrating, in outline, the image processing performed by the image processing unit 82A according to the modification of the first embodiment. In FIG. 7, Step S201 to Step S206 are associated with Step S101 to Step S106 described above with reference to FIG. 5, respectively.

At Step S207, the determination unit 826 determines whether or not the amount of the core tissue area calculated by performing an arithmetic operation by the arithmetic unit 825 is larger than or equal to the threshold. If it is determined, by the determination unit 826, that the amount of the core tissue area calculated by performing the arithmetic operation by the arithmetic unit 825 is larger than or equal to the threshold (Yes at Step S207), the image processing system 1A proceeds to Step S208 that will be described later. In contrast, if it is determined, by the determination unit 826, that the amount of the core tissue area calculated by performing the arithmetic operation by the arithmetic unit 825 is not larger than or equal to the threshold (No at Step S207), the image processing system 1A proceeds to Step S209 that will be described later.

At Step S208, the display controller 823 causes the display unit 6 to display information indicating that the amount of the core tissue of the specimen SP is normal. After the process at Step S208, the image processing system 1A returns to the main routine described above with reference to FIG. 4, and ends the present image processing process.

At Step S209, the display controller 823 causes the display unit 6 to display a warning indicating that the amount of the core tissue of the specimen SP will be insufficient. After the process at Step S209, the image processing system 1A returns to the main routine described above with reference to FIG. 4, and ends the present image processing process.

According to the modification of the first embodiment described above, the determination unit 826 determines whether or not the amount of the core tissue area calculated by performing the arithmetic operation by the arithmetic unit 825 is larger than or equal to the threshold, so that it is possible to determine, with a simple operation, whether or not the amount of the tissue of the core tissue that is needed for pathological diagnosis and that is included in the specimen SP obtained from a biopsy is sufficient.

Furthermore, according to the modification of the first embodiment, the display controller 823 causes the display unit 6 to display the warning indicating that the amount of the core tissue of the specimen SP will be insufficient, so that the evaluator or the user is able to intuitively grasp the amount of the core tissue of the specimen SP.

Furthermore, according to the modification of the first embodiment, the display controller 823 causes the display unit 6 to display the warning indicating that the amount of the core tissue of the specimen SP will be insufficient, so that proficiency of the evaluator or the user is not needed and it is thus possible to reduce the working hours.

Second Embodiment

In the following, a second embodiment will be described. In the first embodiment described above, the spectral transmittance of the core tissue is manually set by the user operating the operating unit 7, and an area is extracted in accordance with this setting result; however, in the second embodiment, the spectral transmittance of the core tissue is manually set, and an area is extracted in accordance with this setting result. Furthermore, components that are identical to those in the image processing system 1 according to the first embodiment are assigned the same reference numerals and descriptions thereof in detail will be omitted.

Configuration of Image Processing System

Figure 8:
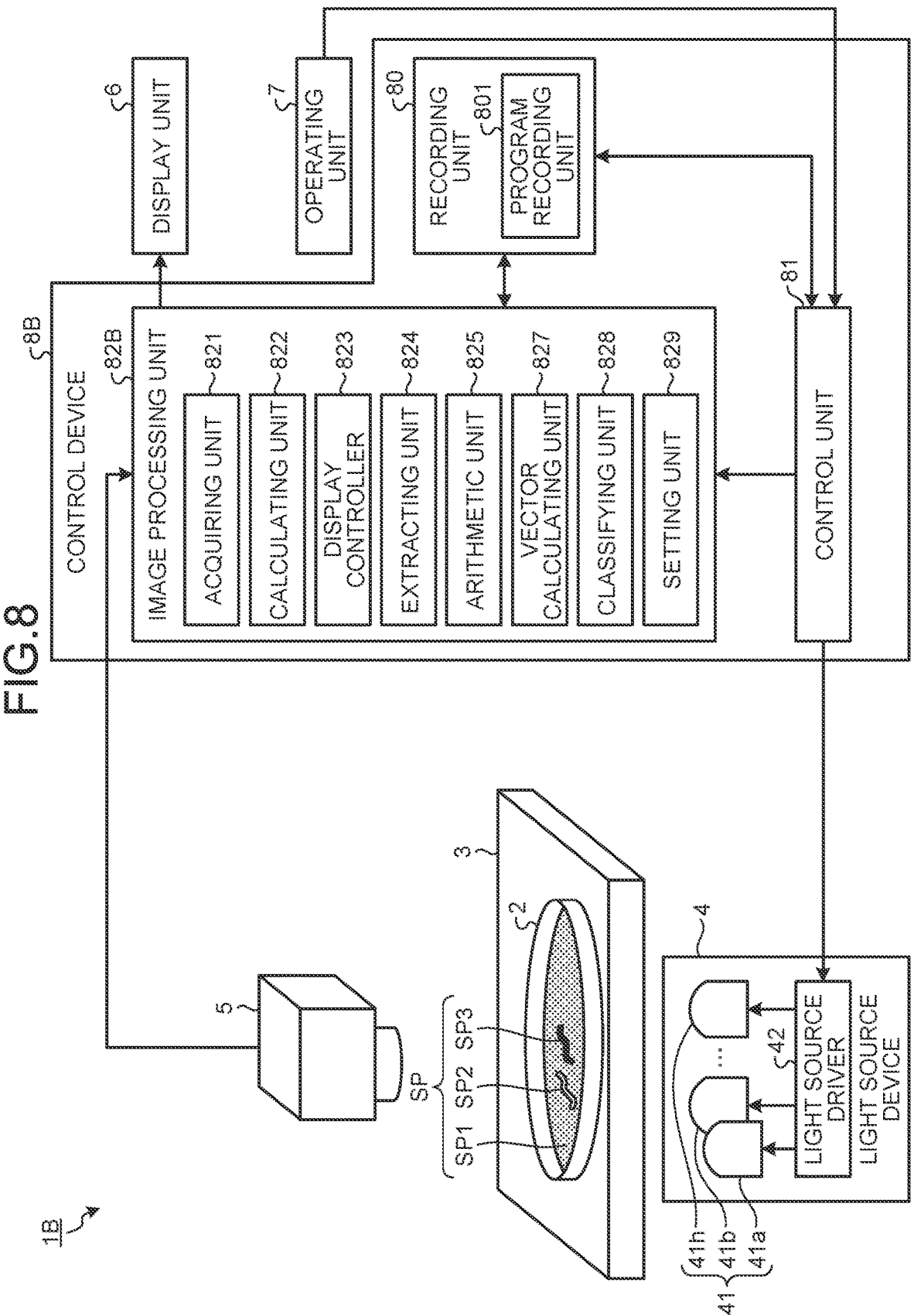
FIG. 8 is a schematic diagram illustrating a schematic configuration of an image processing system according to a second embodiment.

FIG. 8 is a schematic diagram illustrating a schematic configuration of an image processing system according to the second embodiment. An image processing system 1B illustrated in FIG. 8 includes a control device 8B instead of the control device 8 included in the image processing system according to the first embodiment described above. Furthermore, the control device 8B includes an image processing unit 82B instead of the image processing unit 82 included in the control device 8 according to the first embodiment described above.

The image processing unit 82B is constituted by using a memory and a processor including hardware, such as a FPGA or a GPU. The image processing unit 82A further includes, in addition to the configuration according to the first embodiment described above, a vector calculating unit 827, a classifying unit 828, and a setting unit 829.

The vector calculating unit 827 calculates a spectral vector of each of the pixels included in the spectral transmittance image.

The classifying unit 828 classifies each of the pixels included in the spectral transmittance image into at least two or more groups on the basis of the degree of similarity between the spectral vector of each of the pixels calculated by the vector calculating unit 827 and a reference vector. The classifying unit 828 classifies, on the basis of the degree of similarity between the spectral vector of each of the pixels and each of plurality of reference vectors, each of the pixels included in the spectral transmittance image into three or more groups.

The setting unit 829 sets, from among a plurality of blocks obtained by dividing the spectral transmittance image into each of predetermined pixels, an area of a block that has a large number of pixels that belongs to a group that has a high degree of similarity to the reference vector as the reference area. Furthermore, the setting unit 829 sets the reference areas of each of the plurality of reference vectors.

Process Performed by Image Processing System

Figure 9:
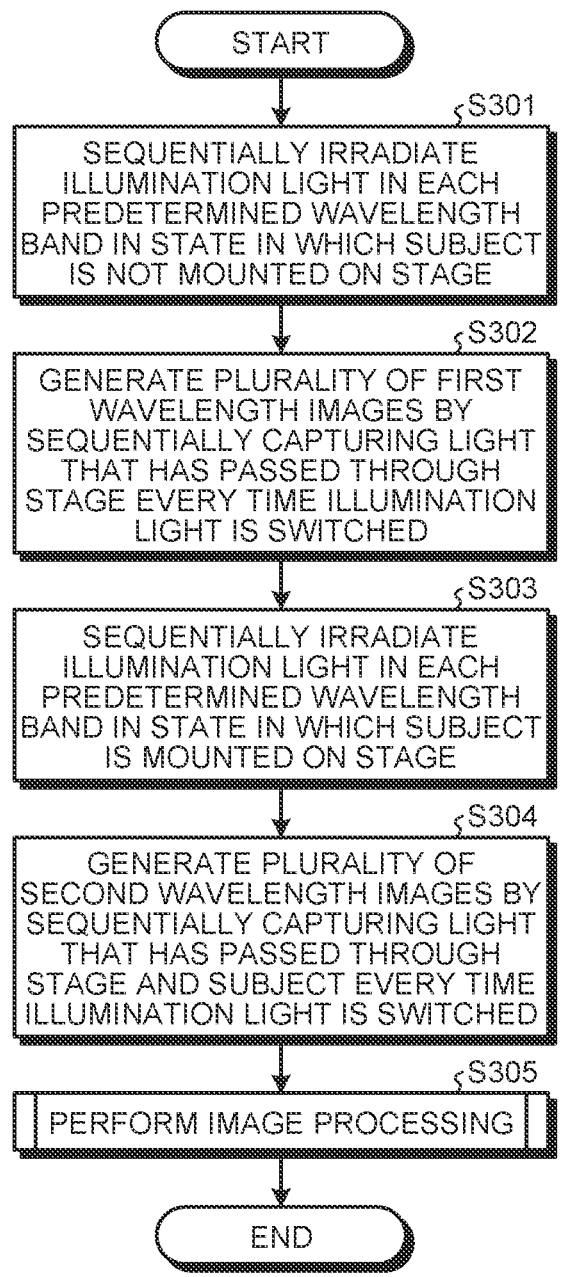
FIG. 9 is a flowchart illustrating, in outline, a process performed by the image processing system according to the second embodiment.

In the following, a process performed by the image processing system 1B will be described. FIG. 9 is a flowchart illustrating, in outline, the process performed by the image processing system 1B.

As illustrated in FIG. 9, first, the control unit 81 causes the light source device 4 to sequentially irradiate the illumination light in each of the predetermined wavelength bands in a state in which the specimen vessel 2 is not mounted on the stage 3 (Step S301), and causes the imaging device 5 to sequentially capture the light that has passed through the stage 3, whereby a plurality of the first wavelength images is generated (Step S302).

Subsequently, the control unit 81 causes the light source device 4 to sequentially irradiate illumination light in each of the predetermined wavelength bands in a state in which the specimen vessel 2 is mounted on the stage (Step S303), and causes the imaging device 5 to sequentially capture the light that has passed through both of the stage and the specimen SP, whereby the second wavelength image is generated (Step S304).

After that, the image processing unit 82B performs image processing for determining whether or not the amount of the tissue of the core tissue included in the specimen SP contained in the specimen vessel 2 is larger than or equal to the threshold (Step S305). After the process performed at Step S305, the image processing system 1B ends the present image processing process.

Image Processing

Figure 10:
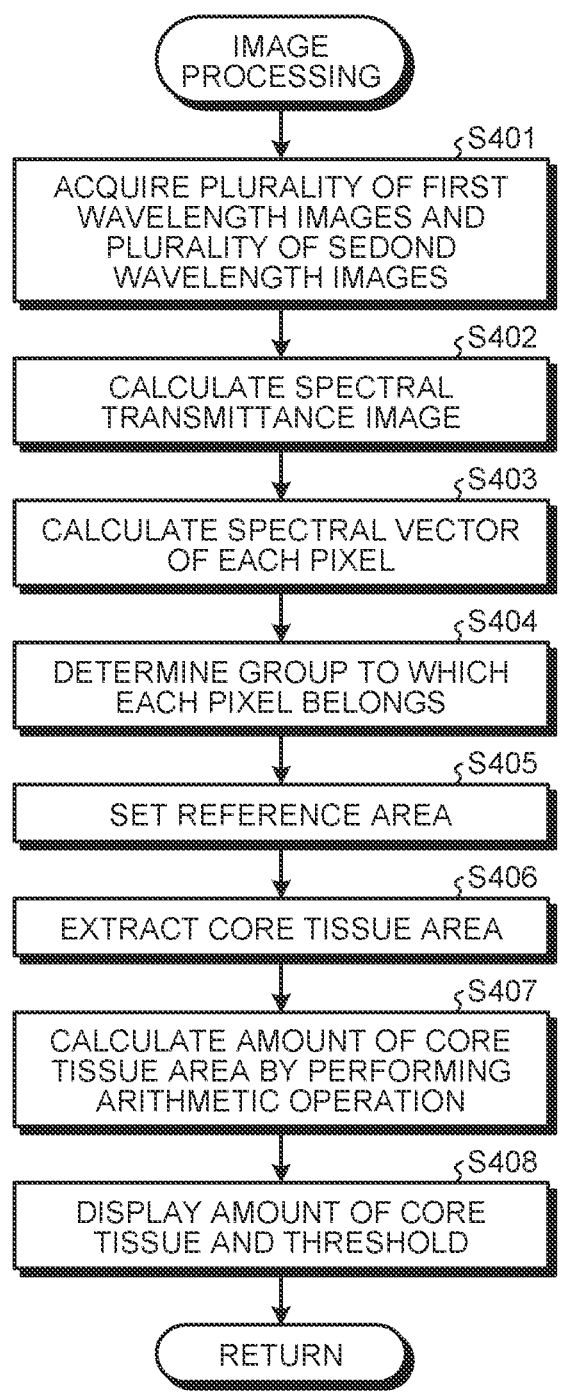
FIG. 10 is a flowchart illustrating, in outline, image processing performed in the process illustrated in FIG. 9.

FIG. 10 is a flowchart illustrating, in outline, the image processing performed at Step S305 described above.

As illustrated in FIG. 10, first, the acquiring unit 821 acquires the plurality of first wavelength images and the plurality of second wavelength images both of which are sequentially generated by the imaging device 5 (Step S401).

Subsequently, the calculating unit 822 calculates the spectral transmittance image in each of the wavelength bands of the illumination light on the basis of the ratio between each of the wavelengths of the first wavelength images and each of the wavelengths of the second wavelength images in each of the wavelength bands of the illumination light (Step S402).

After that, the vector calculating unit 827 calculates a spectral vector of each of the pixels included in the spectral transmittance image (Step S403). Specifically, the vector calculating unit 827 calculates a spectral vector x [i,j][k] of each of the pixels included in the spectral transmittance image. Here, [i,j] denotes a pixel position of the spectral transmittance image (i denotes a pixel position in the horizontal direction and j denotes a pixel position in the vertical direction), and k denotes the number of dimensions of a vector.

Subsequently, the classifying unit 828 classifies each of the pixels included in the spectral transmittance image into at least two or more groups on the basis of the degree of similarity between the spectral vector of each of the pixels calculated by the vector calculating unit 827 and the reference vector (Step S404). Specifically, the classifying unit 828 calculates the degree of similarity between the reference vector and the pixel at the subject position obtained by using Expression (1) below, where the spectral vector of the pixel at the subject position is denoted by x, the reference vector at the reference position is denoted by y, and the range of the wavelength band (range of the band) of the illumination light is denoted by v.

$$\frac{\vec{x}\cdot\vec{y}}{|\vec{x}||\vec{y}|} = \frac{\vec{x}}{|\vec{x}|}\cdot\frac{\vec{y}}{|\vec{y}|} = \frac{\sum_{i=1}^{|v|} x_i y_i}{\sqrt{\sum_{i=1}^{|v|} x_i^2}\sqrt{\sum_{i=1}^{|v|} x_i^2}} \quad (1)$$

More specifically, the classifying unit 828 performs, by using Expression (1), a clustering process on the spectral vector x [i,j][k] of all of the pixels, and classifies the pixels into at least three clusters A, B, and C. Then, the classifying unit 828 performs classification by comparing the spectral vectors at the position of the center of gravity of the three clusters of A, B, and C to the reference vectors of Red [k], White [k], and Background [k], and by determining which of the cluster A, the cluster B, and the cluster C corresponds to one of the red tissue, the white tissue, and the background. Here, Red [k] that is the reference vector indicates the spectral transmittance vector of the red tissue that corresponds to the core tissue of the specimen SP that is detected as clinical data in advance, White [k] indicates the spectral transmittance vector of the white tissue other than the core tissue of the specimen SP that is detected as clinical data in advance, and Background [k] indicates the spectral transmittance vector of the background (blood plasma or a tissue fluid) that is detected as clinical data in advance. In the following, the classifying unit 828 classifies the cluster A as the red tissue, the cluster B as the white tissue, and the cluster C as the background. Then, the classifying unit 828 divides the entire of the spectral transmittance image into blocks having a predetermined size of, for example, 8×8 pixels, and searches for the block that has a largest number of pixels belonging to the cluster A as a[r]. Furthermore, the classifying unit 828 searches for the block that has a largest number of pixels belonging to the cluster B relative to the entire of the spectral transmittance image as b[s], and searches for the block that has a largest number of pixels belonging to the cluster C as c[t]. Here, r, s, t each denote the number of pixels. After that, if r is 1 with respect to a[r], the classifying unit 828 defines the subject block as a cluster A, that is, the reference position (reference area) of the red tissue. Furthermore, if r is larger than or equal to 1, the classifying unit 828 defines the block having the highest degree of similarity to Red[k] related to the average vector of each of the blocks as the reference position (reference area) of the red tissue. The classifying unit 828 performs the same process described above on b[s] and c[t], and defines as the reference positions (reference areas) of the white tissue and the background, respectively.

After that, the setting unit 829 sets, from among the plurality of blocks obtained by dividing the spectral transmittance image into each of predetermined pixels, an area of the block (reference area) that has a large number of pixels that belongs to the group that has a high degree of similarity to the reference vector as an reference area (Step S405).

Subsequently, the extracting unit 824 extracts, as the core tissue area, the reference area that has been set by the setting unit 829 (Step S406).

After that, the arithmetic unit 825 calculates, by performing an arithmetic operation, an amount of the core tissue area extracted by the extracting unit 824 (Step S407). For example, the arithmetic unit 825 calculates, by performing an arithmetic operation, the square measure of the core tissue area included in the specimen SP by using the square measure of the pixels that are extracted as the core tissue area from among the pixels on the image sensor included in the imaging device 5 and using the magnification of the optical system included in the imaging device 5, and then, calculates, by performing an arithmetic operation, a value of this square measure as the amount of the core tissue area.

Subsequently, the display controller 823 causes the display unit 6 to display the amount of the core tissue of the specimen SP calculated by performing the arithmetic operation performed by the arithmetic unit 825 and the threshold (Step S408). As a result, it is possible for an evaluator or a user to intuitively determine, with a simple operation, whether or not the amount of the tissue of the core tissue that is needed for pathological diagnosis and that is included in the specimen SP obtained from a biopsy is sufficient. After the process at Step S408, the image processing system 1B returns to the main routine illustrated in FIG. 9, and ends the present image processing process.

According to the second embodiment described above, the setting unit 829 sets, from among the plurality of blocks obtained by dividing the spectral transmittance image into each of predetermined pixels, an area of the block that has a large number of pixels that belongs to a group that has a high degree of similarity to the reference vector as the reference area, so that it is possible to automatically determine, with a simple operation, whether or not the amount of the core tissue that is needed for pathological diagnosis and that is included in the specimen obtained from a biopsy is sufficient.

Furthermore, according to the second embodiment, the classifying unit 828 classifies, on the basis of the degree of similarity between the spectral vector of each of the pixels calculated by the vector calculating unit 827 and the reference vector, each of the pixels of the spectral transmittance image into at least two or more groups, so that it is possible to accurately perform segmentation of blood, the white tissue, the red tissue, and the background.

Furthermore, according to the second embodiment, the display controller 823 causes the display unit 6 to display the amount of the amount of core tissue of the specimen SP and the threshold, so that the evaluator or the user is possible to intuitively grasp the amount of the core tissue of the specimen SP.

Furthermore, according to the second embodiment, the display controller 823 causes the display unit 6 to display the amount of the amount of the core tissue of the specimen SP and the threshold, so that proficiency of the evaluator or the user is not needed, it is thus possible to reduce working hours.

Furthermore, according to the second embodiment, as the multiband illumination light irradiated by the light source device 4, illumination light that includes at least one narrow band light in a wavelength band in which a full width at half maximum is within a range of 30 nm, for example, illumination light that includes a narrow band in a wavelength band of one of 415 nm, 430 nm, 465 nm, 505 nm, 545 nm, 600 nm, 630 nm, 660 nm, and 700 nm as a peak, is irradiated; therefore, in a case of, for example, 600 nm, it is possible to display the boundary between blood and solid tissue at a high contrast, and, in a case of 505 nm, if the color of blood is light, it is possible to display the boundary between the background and solid tissue at a high contrast.

Modification of the Second Embodiment

In the following, in the second embodiment described above, by displaying the amount of the core tissue area calculated by performing the arithmetic operation performed by the arithmetic unit 825 and the threshold on the display unit 6, whether or not the amount of the core tissue area is sufficient is determined by the evaluator or the user; however, in a modification according to the second embodiment, determination is performed by a control device. In a description below, a configuration of an image processing system according to the modification of the second embodiment is described, and then, image processing performed by an image processing system according to the modification of the second embodiment will be described. Furthermore, components that are identical to those in the image processing system 1B according to the second embodiment are assigned the same reference numerals and descriptions thereof in detail will be omitted.

Configuration of Image Processing System

Figure 11:
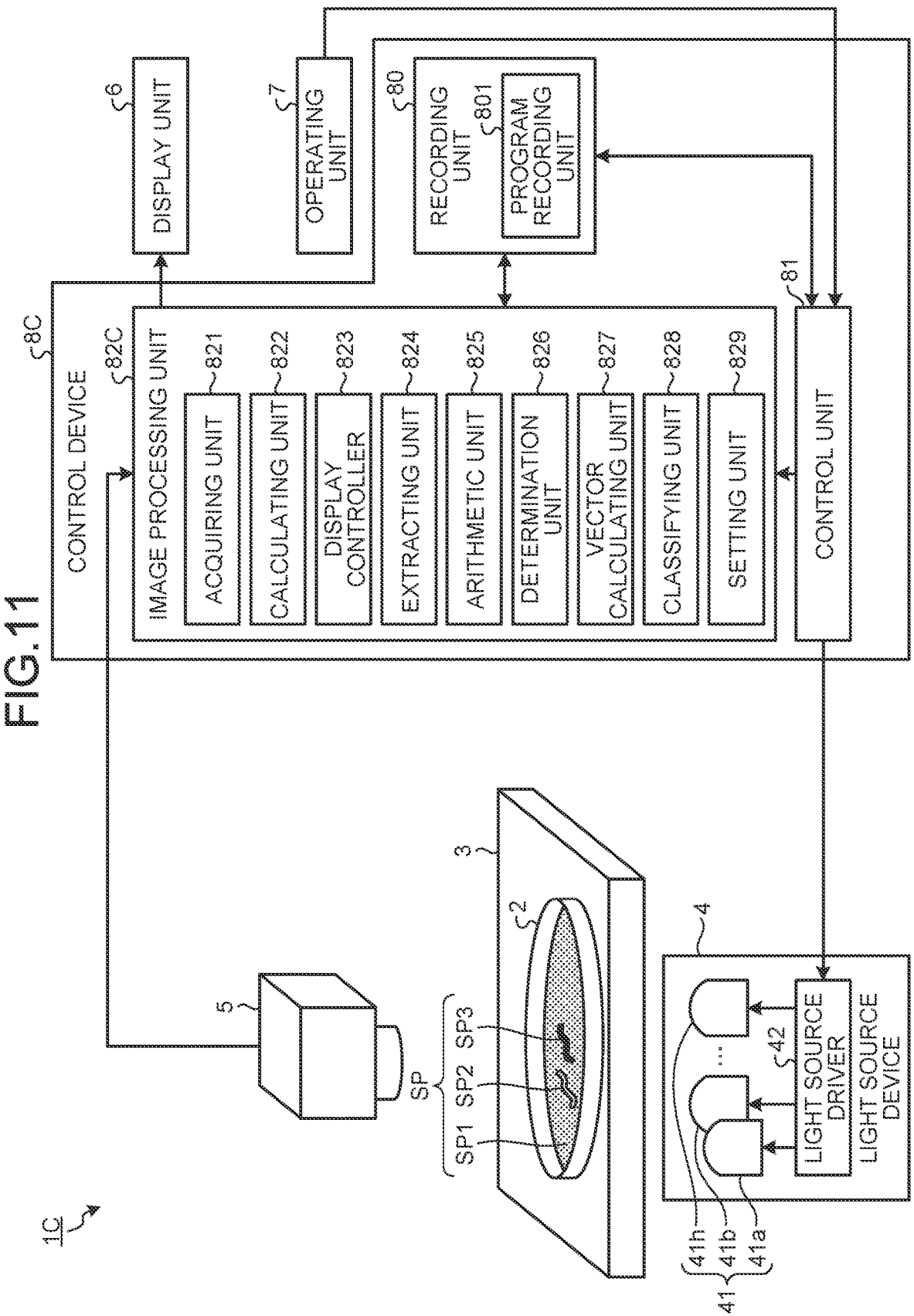
FIG. 11 is a schematic diagram illustrating a schematic configuration of an image processing system according to an modification of the second embodiment.

FIG. 11 is a schematic diagram illustrating a schematic configuration of the image processing system according to the modification of the second embodiment. An image processing system 1C illustrated in FIG. 11 includes a control device 8C instead of the control device 8B according to the second embodiment described above. The control device 8C includes an image processing unit 82C instead of the image processing unit 82B according to the first embodiment described above.

The image processing unit 82C is configured by using a memory and a processor including hardware, such as a FPGA or a GPU. The image processing unit 82C further includes the determination unit 826 according to the modification of the first embodiment described above.

Image Processing

Figure 12:
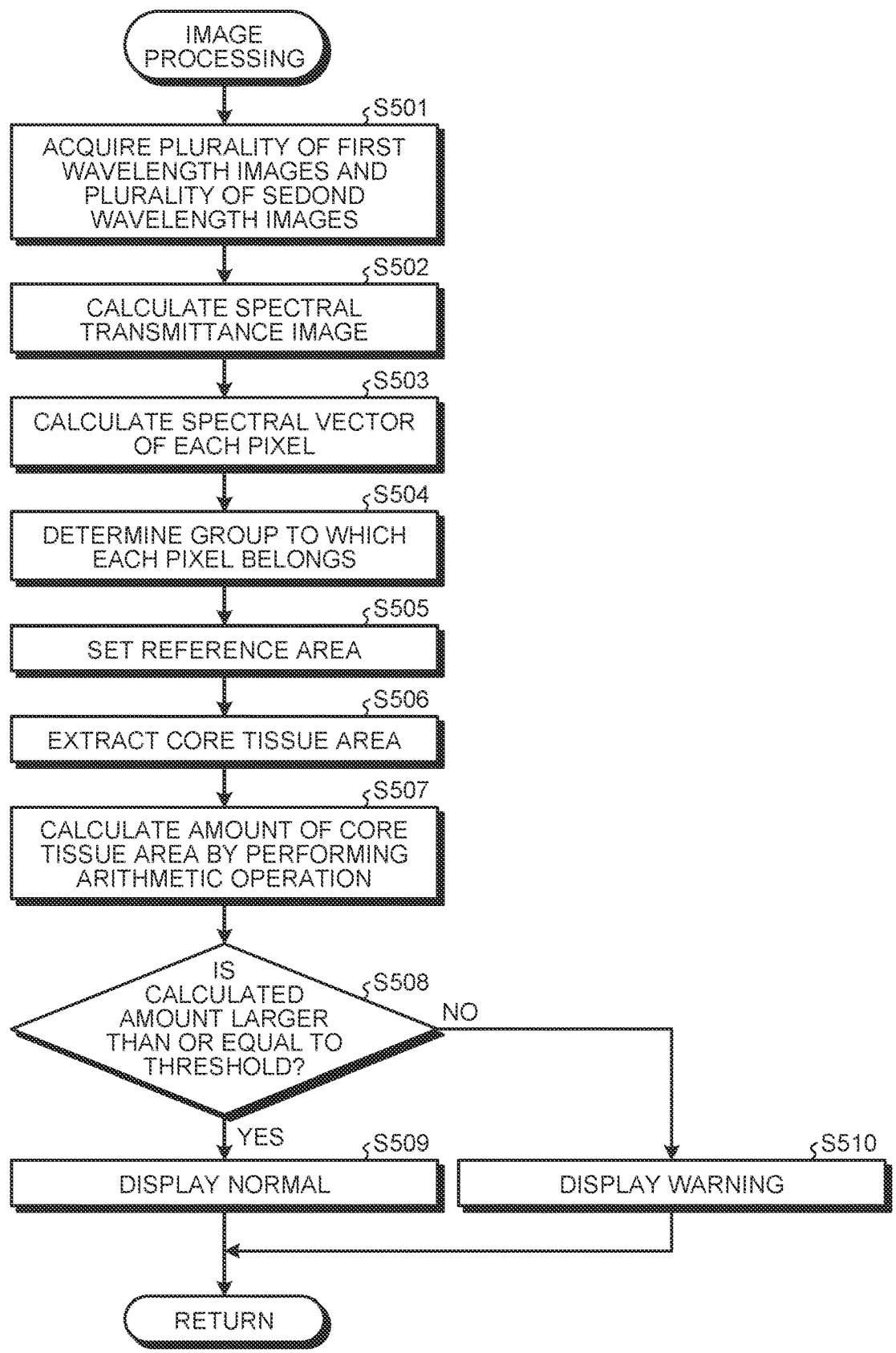
FIG. 12 is a flowchart illustrating, in outline, image processing performed by an image processing unit according to the modification of the second embodiment.

FIG. 12 is a flowchart illustrating, in outline, the image processing performed by the image processing unit 82C according to the modification of the second embodiment.

The processes performed at Step S501 to Step S507 are associated with the processes performed at Step S401 to Step S407 described above with reference to FIG. 10, respectively.

At Step S508, the determination unit 826 determines whether or not the amount of the core tissue area calculated by performing an arithmetic operation performed by the arithmetic unit 825 is larger than or equal to the threshold. If it is determined, by the determination unit 826, that the amount of the core tissue area calculated by performing the arithmetic operation performed by the arithmetic unit 825 is larger than or equal to the threshold (Yes at Step S508), the image processing system 1C proceeds to Step S509 that will be described later. In contrast, if it is determined, by the determination unit 826, that the amount of the core tissue area calculated by performing the arithmetic operation performed by the arithmetic unit 825 is not larger than or equal to the threshold (No at Step S508), the image processing system 1C proceeds to Step S310 that will be described later. Furthermore, in addition to the core tissue, the determination unit 826 may also determine whether or not an amount of white tissue is larger than or equal to the threshold.

At Step S509, the display controller 823 causes the display unit 6 to display information indicating that the amount of the core tissue of the specimen SP is normal. After Step S509, the image processing system 1C returns to the main routine described above with reference to FIG. 9, and ends the present image processing process.

At Step S510, the display controller 823 causes the display unit 6 to display a warning indicating that the amount of the core tissue of the specimen SP will be insufficient. After Step S510, the image processing system 1A returns to the main routine described above with reference to FIG. 9, and ends the present image processing process.

Furthermore, according to the second embodiment, the display controller 823 causes the display unit 6 to display the warning indicating that the amount of the core tissue of the specimen SP will be insufficient, so that the evaluator or the user is possible to intuitively grasp the amount of the core tissue of the specimen SP.

Furthermore, according to the second embodiment, the display controller 823 causes the display unit 6 to display a warning indicating that the amount of the core tissue of the specimen SP will be insufficient, so that proficiency of the evaluator or the user is not needed, and it is thus possible to reduce working hours.

Other Embodiments

Various modes may be made by appropriately combining a plurality of components disclosed in the first and the second embodiments and the modifications thereof described above. For example, some components may also be omitted from all of the components described above in the first and the second embodiments and the modifications thereof. Furthermore, the components described above in the first and the second embodiments and the modifications thereof may also be appropriately combined.

Furthermore, in the first and the second embodiments and the modifications thereof, the light source device, the imaging device, the display unit, the operating unit, and the control device are separately constituted; however, these components may be integrally constituted.

Furthermore, in the first and the second embodiments and the modifications thereof, each of the control devices 8, 8A, 8B, and 8C is connected to the imaging device 5 in a wired manner. However, the configuration is not limited to this, and, for example, it may also be possible to configure so as to be able to communicate with each other by using wireless communication in both directions. That is, by disposing only the stage 3, the light source device 4, and the imaging device 5 at a clinical site and by disposing one of the control devices 8, 8A, 8B, and 8C, the display unit 6, and the operating unit 7 are disposed in another room, such as an observation room, it may also determine the amount of the core tissue of the specimen SP by performing wireless communication or wire communication in both directions.

Furthermore, in the first and the second embodiments and the modifications thereof, the first wavelength image is generated such that the imaging device 5 captures the state in which the specimen SP is not mounted on the stage 3; however, for example, it may be possible to cause the recording unit 80 to record the first wavelength image, and the calculating unit 822 may generate the spectral transmittance image by using the first wavelength image that is caused to be recorded by the recording unit 80.

Furthermore, in the first and the second embodiments and the modifications thereof, the "components" described above can be read as "means", "circuits", or the like. For example, a control unit can be read as a control means or a control circuit.

Furthermore, a program to be executed by the image processing system according to the first and the second embodiments and the modifications thereof is provided by being recorded in a computer readable recording medium, such as a CD-ROM, a flexible disk (FD), a CD-R, a digital versatile disk (DVD), a USB medium, or a flash memory, as file data in the form that can be installed or that can be executed.

Furthermore, a program to be executed by the image processing system according to the first and the second embodiments and the modifications thereof may also be configured such that the program is stored in a computer connected to a network, such as the Internet, and is provided by being downloaded via a network. Furthermore, the program to be executed by a specimen analysis device according to the present disclosure may also be configured such that the program is provided or distributed via a network, such as the Internet.

Furthermore, in a description of the flowcharts in the application, the relationship between before and after the processes performed at each step is stated by using "first", "then", "subsequently", and the like; however, the order of the processes needed to implement the disclosure is not uniquely determined by the descriptions above. Specifically, the order of the processes in the flowcharts described in the application may also be changed as long as processes do not conflict with each other.

According to the present disclosure, an advantage is provided in that it is possible to determine whether or not an amount of core tissue that is needed for pathological diagnosis and that is included in a specimen obtained from a biopsy is sufficient.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising a processor comprising hardware, the processor being configured to:
    acquire a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;
    calculate a spectral transmittance image based on the first wavelength image and the second wavelength image;
    cause a display to display at least one of the spectral transmittance image and the second wavelength image as a display image;
    extract, based on a designation signal for designating a reference area in the display image, an area of the spectral transmittance image having spectral transmittance similar to spectral transmittance of the reference area as a core tissue area of the core tissue; and
    calculate an amount of the core tissue area.

2. The image processing apparatus according to claim 1, wherein the processor is further configured to cause the display to display the amount of the core tissue area and a threshold.

3. The image processing apparatus according to claim 1, wherein the processor is further configured to
    determine whether or not an amount of the core tissue area is larger than or equal to a threshold, and
    cause the display to display, when it is determined that the amount of the core tissue area is not larger than or equal to the threshold, a warning indicating that an amount of the core tissue is abnormal.

4. The image processing apparatus according to claim 1, wherein
    the first wavelength image is one of a plurality of first wavelength images,
    the second wavelength image is one of a plurality of second wavelength images,
    the processor is further configured to
    acquire the plurality of first wavelength images and the plurality of second wavelength images, the plurality of first wavelength images being generated by sequentially irradiating the stage configured to transmit light with multiband illumination light in each of predetermined wavelength bands and by sequentially capturing light that has passed through the stage, the plurality of second wavelength images being generated by sequentially irradiating the specimen that is in the state of being mounted on the stage with the multiband illumination light in each of the predetermined wavelength bands and by sequentially capturing the light that has passed through the stage and the specimen, and
    calculate the spectral transmittance image based on a ratio between each of wavelengths of the plurality of first wavelength images and each of wavelengths of the plurality of second wavelength images.

5. An image processing system comprising:
    the image processing apparatus according to claim 1;
    a light source configured to irradiate illumination light in a wavelength band in a switchable manner;
    an imager configured to capture light that has passed through the stage; and a controller configured to
cause the first wavelength image to be generated by causing the light source to irradiate the illumination light in a state in which the specimen is not mounted on the stage and by causing the imager to capture an image, and
cause the second wavelength image to be generated by causing the light source to irradiate the illumination light in the state in which the specimen is mounted on the stage and by causing the imager to capture an image.

6. The image processing system according to claim 5, wherein the light source is configured to irradiate illumination light that includes at least one narrow band light in a wavelength band in which a full width at half maximum is within a range of 30 nm.

7. The image processing system according to claim 6, wherein the narrow band light is in a wavelength band of one of 415 nm, 430 nm, 465 nm, 505 nm, 545 nm, 600 nm, 630 nm, 660 nm, and 700 nm as a peak.

8. An image processing apparatus comprising a processor comprising hardware, the processor being configured to:
acquire a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;
calculate a spectral transmittance image based on the first wavelength image and the second wavelength image;
calculate a spectral vector of each of pixels included in the spectral transmittance image;
classify each of the pixels included in the spectral transmittance image into at least two or more groups based on a degree of similarity between the spectral vector of each of the pixels and a reference vector;
set, from among a plurality of blocks obtained by dividing the spectral transmittance image into each of predetermined pixels, an area of a block that has a large number of pixels that belongs to a group that has a high degree of similarity to the reference vector as a reference area;
extract an area of the spectral transmittance image having spectral transmittance similar to spectral transmittance of the reference area as a core tissue area of the core tissue; and
calculate an amount of the core tissue area.

9. The image processing apparatus according to claim 8, wherein
the processor is further configured to
classify, based on a degree of similarity between the spectral vector of each of the pixels and each of a plurality of reference vectors, each of the pixels included in the spectral transmittance image into three or more groups, and
set the reference area of each of the plurality of reference vectors.

10. The image processing apparatus according to claim 8, wherein the processor is further configured to cause a display to display the amount of the core tissue area and a threshold.

11. The image processing apparatus according to claim 8, wherein the processor is further configured to
determine whether or not the amount of the core tissue area is greater than or equal to a threshold, and
cause a display to display, when it is determined that the amount of the core tissue area is not larger than or equal to the threshold, a warning indicating that an amount of the core tissue is abnormal.

12. The image processing apparatus according to claim 8, wherein
the first wavelength image is one of a plurality of first wavelength images,
the second wavelength image is one of a plurality of second wavelength images,
the processor is further configured to
acquire the plurality of first wavelength images and the plurality of second wavelength images, the plurality of first wavelength images being generated by sequentially irradiating the stage configured to transmit light with multiband illumination light in each of predetermined wavelength bands and by sequentially capturing light that has passed through the stage, the plurality of second wavelength images being generated by sequentially irradiating the specimen that is in the state of being mounted on the stage with the multiband illumination light in each of the predetermined wavelength bands and by sequentially capturing the light that has passed through the stage and the specimen, and
calculate the spectral transmittance image based on a ratio between each of wavelengths of the plurality of first wavelength images and each of wavelengths of the plurality of second wavelength images.

13. An image processing system comprising:
the image processing apparatus according to claim 8;
a light source configured to irradiate illumination light in a wavelength band in a switchable manner;
an imager configured to capture light that has passed through the stage; and
a controller configured to
cause the first wavelength image to be generated by causing the light source to irradiate the illumination light in a state in which the specimen is not mounted on the stage and by causing the imager to capture an image, and
cause the second wavelength image to be generated by causing the light source to irradiate the illumination light in the state in which the specimen is mounted on the stage and by causing the imager to capture an image.

14. The image processing system according to claim 13, wherein the light source is configured to irradiate illumination light that includes at least one narrow band light in a wavelength band in which a full width at half maximum is within a range of 30 nm.

15. The image processing system according to claim 14, wherein the narrow band light is in a wavelength band of one of 415 nm, 430 nm, 465 nm, 505 nm, 545 nm, 600 nm, 630 nm, 660 nm, and 700 nm as a peak.

16. An image processing method performed by an image processing apparatus, the method comprising:
acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;

calculating a spectral transmittance image based on the first wavelength image and the second wavelength image;

causing a display to display at least one of the spectral transmittance image and the second wavelength image as a display image;

extracting, based on a designation signal for designating a reference area in the display image, an area of the spectral transmittance image having spectral transmittance similar to spectral transmittance of the reference area as a core tissue area of the core tissue; and calculating an amount of the core tissue area.

17. An image processing method performed by an image processing apparatus, the method comprising:

acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;

calculating a spectral transmittance image based on the first wavelength image and the second wavelength image;

calculating a spectral vector of each of pixels included in the spectral transmittance image;

classifying each of the pixels included in the spectral transmittance image into at least two or more groups based on a degree of similarity between the spectral vector of each of the pixels and a reference vector;

setting, from among a plurality of blocks obtained by dividing the spectral transmittance image into each of predetermined pixels, an area of a block that has a large number of pixels that belongs to a group that has a high degree of similarity to the reference vector as a reference area;

extracting an area of the spectral transmittance image having spectral transmittance similar to spectral transmittance of the reference area as a core tissue area of the core tissue; and calculating an amount of the core tissue area.

18. A non-transitory computer-readable recording medium with an executable program stored thereon, the program causing an image processing apparatus to perform:

acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;

calculating a spectral transmittance image based on the first wavelength image and the second wavelength image;

causing a display to display at least one of the spectral transmittance image and the second wavelength image as a display image;

extracting, based on a designation signal for designating a reference area in the display image, an area of the spectral transmittance image having spectral transmittance similar to spectral transmittance of the reference area as a core tissue area of the core tissue; and calculating an amount of the core tissue area.

19. A non-transitory computer-readable recording medium with an executable program stored thereon, the program causing an image processing apparatus to perform:

acquiring a first wavelength image and a second wavelength image, the first wavelength image being generated by irradiating a stage configured to transmit light with illumination light in a predetermined wavelength band and by capturing light that has passed through the stage, the second wavelength image being generated by irradiating a specimen that is in a state of being mounted on the stage with the illumination light in the predetermined wavelength band and by capturing light that has passed through the stage and the specimen, the specimen being obtained from a biopsy and including a core tissue;

calculating a spectral transmittance image based on the first wavelength image and the second wavelength image;

calculating a spectral vector of each of pixels included in the spectral transmittance image;

classifying each of the pixels included in the spectral transmittance image into at least two or more groups based on a degree of similarity between the spectral vector of each of the pixels and a reference vector;

setting, from among a plurality of blocks obtained by dividing the spectral transmittance image into each of predetermined pixels, an area of a block that has a large number of pixels that belongs to a group that has a high degree of similarity to the reference vector as a reference area;

extracting an area of the spectral transmittance image having spectral transmittance similar to spectral transmittance of the reference area as a core tissue area of the core tissue; and calculating an amount of the core tissue area.

* * * * *